United States Patent [19]

Herrmann et al.

[11] Patent Number: 5,039,679

[45] Date of Patent: Aug. 13, 1991

[54] CERTAIN DERIVATIVES OF 1,4-DIHYDRO-5-ISOPROPOXY-1,6-NAPHTHYRIDINE-3-CARBOXYLIC ACID, PHARMACEUTICAL COMPOSITIONS CONTAINING THEM, AND METHODS OF USING THEM

[75] Inventors: Wolfgang Herrmann, Merzhausen; Jürgen Kleinschroth, Denzlingen; Klaus Steiner, Waldkirch, all of Fed. Rep. of Germany

[73] Assignee: Goedecke Aktiengesellschaft, Berlin, Fed. Rep. of Germany

[21] Appl. No.: 480,430

[22] Filed: Feb. 15, 1990

[30] Foreign Application Priority Data

Mar. 1, 1989 [DE] Fed. Rep. of Germany ....... 3906406

[51] Int. Cl.[5] .................... A61K 31/435; C07D 471/04

[52] U.S. Cl. ...................................... 514/300; 546/123

[58] Field of Search ................. 546/123, 321; 514/300

[56] References Cited

U.S. PATENT DOCUMENTS

| | | | |
|---|---|---|---|
| 4,572,909 | 2/1986 | Campbell et al. | 546/321 |
| 4,711,901 | 12/1987 | Satzinger et al. | 546/123 |
| 4,751,228 | 6/1988 | Kleinschroth et al. | 546/123 |
| 4,760,081 | 7/1988 | Satzinger et al. | 546/123 |

*Primary Examiner*—Bernard Dentz

*Attorney, Agent, or Firm*—Elizabeth M. Anderson

[57] ABSTRACT

The present invention concerns the fumaric acid salts of 1,4-dihydro-5-isopropoxy-2-methyl-4-(2-trifluoromethylphenyl) 1,6-naphthyridine-3-carboxylic acid [2-(N-methyl-N-phenylmethylamino)ethyl]ester, processes for preparing them, and pharmaceutical compositions containing them. Methods of using the compounds for treating high blood pressure and diseases of heart and blood vessels.

12 Claims, No Drawings

CERTAIN DERIVATIVES OF 1,4-DIHYDRO-5-ISOPROPOXY-1,6-NAPHTHYRIDINE-3-CARBOXYLIC ACID, PHARMACEUTICAL COMPOSITIONS CONTAINING THEM, AND METHODS OF USING THEM

BACKGROUND OF THE INVENTION

Germany Patent Application 34 31 303, 1,6-naphthyridine derivatives with calcium antagonistic properties are described. (±)-1,4-dihydro-5-isopropoxy-2-methyl-4-(2-trifluoromethylphenyl)-1,6-naphthyridine-3-carboxylic acid [2-(N-methyl-N-phenylmethylamino)-ethyl] ester in the form of the hydrochloride is included. The corresponding U.S. Pat. Nos. are 4,711,901, 4,751,228, and 4,760,081, which are incorporated herein by reference.

SUMMARY OF THE INVENTION

The present invention is concerned with new derivatives of 1,6-naphthyridine-3-carboxylic acid, a process for the preparation thereof, pharmaceutical compositions containing the, and methods of using them. The present invention covers (±)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate and (−)-1,4-dihydro-5-isopropoxy-2-methyl-4-(2-trifluoromethyl-phenyl)-1,6-naphthyridine-3-carboxylic acid [2-(N-methyl-N-phenylmethylamino)-ethyl] ester fumarate. The crystalline form of the (+) isomer is also included.

A pharmaceutical composition comprising a blood pressure lowering amount of (±)-1,4-dihydro-5-isopropoxy-2-methyl-4-(2-trifluoromethylphenyl)-1,6-naphthyridine-3-carboxylic acid [2-N-methyl-N-phenylmethylamino)-ethyl] ester fumarate, (±)-1,4-dihydro-5-isopropoxy-2-methyl-4-(2-trifluoromethyl-phenyl)-1,6-naphthyridine-3-carboxylic acid [2-(N-methyl-N-phenyl-methylamino)-ethyl] ester fumarate, (−)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate, or the crystalline form of (+)-1,4-dihydro-5-isopropoxy-2-methyl-4-(2-trifluoromethylphenyl)1,6-naphthyridine-3-carboxylic acid [2-(N-methyl-N-phenyl-methylamino)-ethyl] ester fumarate together with a pharmaceutically acceptable carrier is also included.

A method for treating high blood pressure using the above compositions is included.

A pharmaceutical composition comprising an effective amount of (±),(+),(−) or the crystalline form of (+) for treating diseases of the heart and blood vessels is also included.

A method for treating diseases of the heart and blood vessels using the above composition is also included.

DETAILED DESCRIPTION

Surprisingly, it has now been found that, in comparison with the other derivatives, the (±) possesses especially marked blood pressure lowering activity. The pharmacological results are even more marked in the case of the optical results which were obtained according to the usual methods of racemate separation. Especially active is (+)-1,4-dihydro-5-isopropoxy-2-methyl-4-(2-trifluoro-methylphenyl)-1,6-naphthyridine-3-carboxylic acid [2-(N-methyl-N-phenylmethylamino)-ethyl] ester.

This ester is an oily base and the hydrochloride displays an instability wit regard to temperature and light, undesirable properties for galenical development and for clinical use. The hydrochloride is unstable even at ambient temperature and a stress test gave, after heating for 2 weeks at 45° C. in the dark, 10% of decomposition products and at ambient temperature in the light 30% of the compound had decomposed after 2 weeks. Furthermore, in animal experiments, an undesirable, very rapid commencement of activity was found which was attributable to the good solubility of the compound in water.

The present invention provides (+)-1,4-dihydro-5-isopropoxy-2-methyl-4-(2-trifluoromethylphenyl)-1,6-naphthyridine-3-carboxylic acid [2-N-methyl-N-phenymethylamino)-ethyl] ester in a crystalline, light- and temperature-stable form for clinical use which, in addition, displays a slower commencement of activity.

Surprisingly, it has been found that the fumarate can be obtained as a crystalline salt with a melting point of 180°–182° C. In addition, it is also stable under the above-mentioned stress conditions (2 weeks at 45° C. in the dark and 2 weeks at ambient temperature in the light). Furthermore, the fumarate also displays a considerable lower water solubility, as can be seen from the following Table 1:

TABLE 1

| | Solubility in | |
|---|---|---|
| Compound | Water | Artificial Gastric Juice |
| Hydrochloride | 20% | 20% |
| Fumarate | 0.1% | 1.5% |

Pharmacological experiments on rats showed that the commencement of activity after oral administration takes place somewhat later in the case of the fumarate than in the case of the hydrochloride, and, in addition, the blood pressure lowering action is, surprisingly, also substantially stronger in the case of the fumarate, as is shown in the following Table 2:

TABLE 2

| Spontaneously Hypertensive Rats | 1 mg/kg PO; n = 6 |
|---|---|
| Hydrochloride | 17% ± 4.4 |
| Fumarate | 26% ± 1.7 |

The present invention is also concerned with the use of the compounds according to the present invention for the treatment of high blood pressure and of heart and blood vessel diseases, as well as with pharmaceutical compositions containing these compounds, optionally together with conventional adjuvant and additive materials.

The compounds according to the present invention can be administered orally or parenterally in liquid or solid form. As injection solution, it is preferable to use water which contains the additives usual in the case of injection solutions, such as stabilizing agents, solubilizing agents, and/or buffers. Such additives include, for example, tartrate and citrate buffers, ethanol, complex formers (such as ethylenediamine-tetraacetic acid and the nontoxic salts thereof), as well as high molecular weight polymers (such as liquid polyethylene oxide) for viscosity regulation. Solid carrier materials include, for example, starch, lactose, mannitol, methylcellulose, talc, highly dispersed silicic acids, high molecular weight fatty acids (such as stearic acid), gelatin, agar-agar, calcium phosphate, magnesium stearate, animal and vegetable fats, and solid high molecular weight polymers (such as polyethylene glycol). Compositions suitable for oral administration can, if desired, also contain sweetening and/or flavoring materials.

1-4-Dihydro-5-isopropoxy-2-methyl-4-(2-trifluoromethylphenyl)-1,6-naphthyridine-3-carboxylic acid [2-(N-methyl-N-phenylmethylamino)-ethyl] ester fumarate can be prepared, for example, by mixing together solutions of the base and of fumaric acid in appropriate solvents or by heating a mixture of equimolar amounts of base and fumaric acid in an appropriate solvent and subsequent crystallization by cooling. As solvents, there can be used, for example, ethyl acetate, lower aliphatic alcohols and lower aliphatic ketones, possibly in admixture with water.

The following Example is given for the purpose of illustrating the present invention:

EXAMPLE 1

400 g (+)-1,4-Dihydro-5-isopropoxy-2-methyl-4-(2-trifluoromethylphenyl)-1,6-naphthyridine-3-carboxylic acid [2-(N-methyl-N-phenylmethylamino)ethyl] ester, together with 8.6 g fumaric acid, are dissolved in 1000 mL ethyl acetate while boiling under reflux. The solution is filtered and the filtrate concentrated to a volume of about 180 mL, a crystalline product thereby precipitating out. This is filtered off with suction and washed with 180 mL ethyl acetate. After drying, the product is dissolved in 300 mL ethanol with gentle warming and thereafter mixed with 1500 mL of water, while stirring. The solution is then allowed to cool to ambient temperature, while stirring. The product which crystallizes out is filtered off with suction and subsequently washed with 100 mL of water. The product is dried in a vacuum to constant weight. Yield: 43.1 g (88.7% of theory); m.p. 180°-182° C.; $[\alpha]_D = 3.8°$ (c=1/methanol); enantiomeric purity 99% (PMR).

EXAMPLE 2

2.9 g (−)-1,4-Dihydro-5-isopropoxy-2-methyl-4-(2-trifluoromethylphenyl)-1,6-naphthyridine-3-carboxylic acid [2-(N-methyl-N-phenylmethylamino)ethyl] ester, together with 0.58 g fumaric acid, are dissolved in 75 mL ethyl acetate while boiling under reflux. The solution is filtered and the filtrate concentrated to a volume of about 20 mL, a crystalline product thereby precipitating out. This is filtered off with suction and washed with 10 mL ethyl acetate. After drying, the product is dissolved in 19.5 mL ethanol with gentle warming and thereafter mixed with 110 mL of water, while stirring. The solution is then allowed to cool to ambient temperature while stirring. The product which crystallizes out is filtered off with suction and subsequently washed with 20 mL of water. The product is dried in a vacuum to constant weight. Yield: 2.1 g (64.2% of theory); m.p. 181°-183° C.; $[\alpha]_D = -3.6°$ (c=1/methanol); enantiomeric purity 99% (PMR).

We claim:

1. A compound named (±)-1,4-dihydro-5-isopropoxy-2-methyl-4-(2-trifluoromethylphenyl)-1,6-naphthyridine-3-carboxylic acid [2-N-methyl-N-phenylmethylamino)-ethyl] ester fumarate.

2. A compound named (±)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate.

3. A compound named (−)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate.

4. Crystalline form of (±)-1,4-dihydro-5-isopropoxy-2-methyl-4-(2-trifluoromethylphenyl)-1,6-naphthyridine-3-carboxylic acid [2-(N-methyl-N-phenylmethylamino)-ethyl] ester fumarate.

5. A pharmaceutical composition comprising a blood pressure lowering amount of (±)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate together with a pharmaceutically acceptable carrier.

6. A method of treating high blood pressure in mammals which comprises administering to said mammal a pharmaceutical composition according to claim 5.

7. A pharmaceutical composition comprising a blood pressure lowering amount of (±)-1,4-dihydro-5-isopropoxy-2-methyl-4-(2-trifluoromethylphenyl)-1,6-naphthyridihe-3-carboxylic acid [2-(N-methyl-N-phenyl-methylamino)-ethyl] ester fumarate together with a pharmaceutically acceptable carrier.

8. A method of treating high blood pressure in mammals which comprises administering to said mammal a pharmaceutical composition according to claim 7.

9. A pharmaceutical composition comprising a blood pressure lowering amount of (−)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate together with a pharmaceutically acceptable carrier.

10. A method of treating high blood pressure in mammals which comprises administering to said mammal a pharmaceutical composition according to claim 9.

11. A pharmaceutical composition for treating blood vessel diseases comprising an effective amount of (±)-1,4-dihydro-5-isopropoxy-2-methyl-4-(2-trifluoromethylphenyl)-1,6-naphthyridine-3-carboxylic acid [2-N-methyl-N-phenylmethylamino)-ethyl] ester fumarate, (±)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate, or (−)-1,4-dihydro-5-isopropoxy-2-methyl-4-(2-trifluoromethylphenyl)-1,6-naphthyridine-3-carboxylic acid [2-(N-methyl-N-phenyl-methylamino)-ethyl] ester fumarate in admixture with a pharmaceutically acceptable carrier.

12. A method for treating heart and blood vessel diseases in mammals which comprises administering to said mammal a pharmaceutical composition according to claim 11.

* * * * *

UNITED STATES PATENT AND TRADEMARK OFFICE

CERTIFICATE OF CORRECTION

PATENT NO. : 5,039,679

DATED : August 13, 1991

INVENTOR(S) : Wolfgang Herrmann et al

It is certified that error appears in the above-identified patent and that said Letters Patent is hereby corrected as shown below:

Column 4, line 3, change "(±)" to "(+)".

Column 4, line 26, change "(±)" to "(+)".

Column 4, line 48, change "(±)" to "(+)".

Signed and Sealed this

Twenty-sixth Day of January, 1993

*Attest:*

STEPHEN G. KUNIN

*Attesting Officer*

*Acting Commissioner of Patents and Trademarks*